(12) United States Patent
Minamikawa

(10) Patent No.: US 6,811,568 B2
(45) Date of Patent: Nov. 2, 2004

(54) ARTIFICIAL JOINT

(75) Inventor: Yoshitaka Minamikawa, Minoo (JP)

(73) Assignees: Aidall International Ltd., Osaka (JP); Nakashima Propeller Co., Ltd., Okayama-Ken (JP)

( * ) Notice: Subject to any disclaimer, the term of this patent is extended or adjusted under 35 U.S.C. 154(b) by 93 days.

(21) Appl. No.: 10/114,788

(22) Filed: Apr. 2, 2002

(65) Prior Publication Data

US 2003/0040805 A1 Feb. 27, 2003

(30) Foreign Application Priority Data

Aug. 27, 2001 (JP) .................................. 2001-256521

(51) Int. Cl.$^7$ ................................................ A61F 2/42
(52) U.S. Cl. ........................... 623/21.15; 623/18.11; 623/21.11; 623/21.16; 623/23.27; 623/23.44; 606/63
(58) Field of Search .................... 623/20.11, 20.34, 623/20.36, 21.11–21.17, 23.26, 23.27, 23.4, 23.44–23.47; 606/62, 63, 18.11

(56) References Cited

U.S. PATENT DOCUMENTS

| | | | |
|---|---|---|---|
| 3,805,302 A | * 4/1974 | Mathys | 623/21.15 |
| 4,013,071 A | * 3/1977 | Rosenberg | 128/92 |
| 4,349,922 A | * 9/1982 | Agee | 623/23.39 |
| 4,759,768 A | * 7/1988 | Hermann et al. | 623/21.15 |
| 4,955,916 A | * 9/1990 | Carignan et al. | 623/21.15 |
| 5,011,497 A | * 4/1991 | Persson et al. | 623/21.15 |
| 5,062,851 A | * 11/1991 | Branemark | 623/21.15 |
| 5,147,386 A | * 9/1992 | Carignan et al. | 623/21.15 |
| 5,425,777 A | * 6/1995 | Sarkisian et al. | 623/21.15 |
| 6,099,571 A | * 8/2000 | Knapp | 623/21.15 |
| 6,475,242 B1 | * 11/2002 | Bramlet | 623/21.11 |
| 6,575,975 B2 | * 6/2003 | Brace et al. | 606/69 |

FOREIGN PATENT DOCUMENTS

| | | | | |
|---|---|---|---|---|
| FR | 2705559 A1 | * 12/1994 | | A61F/2/42 |
| JP | 1984-91956 | 5/1984 | | |
| JP | 1986-276553 | 12/1986 | | |
| JP | 1990-29941 | 8/1990 | | |
| JP | 1997-38122 | 2/1997 | | |
| JP | 2964035 | * 10/1999 | | A61F/2/42 |
| JP | 11332893 | * 12/1999 | | A61F/2/42 |

* cited by examiner

Primary Examiner—David H. Willse
Assistant Examiner—Javier G. Blanco
(74) Attorney, Agent, or Firm—Zito tlp; Joseph J. Zito; Kendal M. Sheets

(57) ABSTRACT

The present invention provides an artificial joint which can be rapidly, securely and easily fixed while being suited to an inner surface of a bone marrow hole by a novel structure absolutely different from the conventional one. An artificial joint is provided with a stem base portion (10) in which a desired head (2) and a desired socket (5) are in slidably contact with each other in a freely bending manner, stems (9, 16) are fitly attached to free ends of the head (2) and the socket (5) respectively, and the respective stems (9, 16) have therein locking screws (14) freely screwing to move along axial directions thereof, and a pair of stem pieces (15) having an elasticity provided to protrude on both front portions of the stem base portion (10), and the locking screws (14) are forcedly inserted within the stem pieces (15) so as to expand them outward, thereby making them tightly contact with and fix to inner surfaces of bone marrow holes (19, 21).

14 Claims, 4 Drawing Sheets

ARTIFICIAL JOINT

BACKGROUND OF THE INVENTION

1. Field of the Invention

The present invention relates to an artificial joint such as an artificial knuckle joint, an artificial elbow joint and the like.

2. Description of the Prior Art

Conventionally, for example, a metacarpophalangeal joint of a finger (hereinafter, refer to an MP joint) is constituted by a metacarpal bone and a proximal phalanx, and a proximal interphalangeal joint (hereinafter, refer to a PIP joint) is constituted by a proximal phalanx and a phalanx media, however, when having an arthritis as typified by a rheumatoid arthritis, particularly joints, ligaments and tendons in hand and foot are gradually affected, so that a painful deformation, a significant limitation of motion or the like appears. As a countermeasure against the matter mentioned above, there has been generally executed an operation of replacing a joint portion deformed due to the arthritis by an artificial joint.

In this case, as the artificial joint mentioned above, there have been disclosed the following structures:

a. a structure in which stems are integrally formed in both ends of a middle flange portion around the middle flange portion with an elastic macromolecule material as typified by a silicon resin.

b. a spherical joint structure obtained by combining a spherical connection end with stems and a spherical surface recessed connection end with stems in a freely bending manner (refer to Japanese Utility Model Publication No. 2-29941 and Japanese Unexamined Patent Publication No. 9-38122).

c. a hinge joint structure obtained by pivoting a connection joint with stems each having an insertion hole by a pin in a freely bending manner (refer to Japanese Unexamined Patent Publication Nos. 59-91956 and 61-276553).

Accordingly, an operation to replace with the artificial joints mentioned above are done in accordance with a method of inserting a stem having a desired shape such as a rod shape, a tapered rod shape or the like into a bone marrow hole and fixing it via a bone cement, or a method of inserting a stem formed so as to fit to a required inner surface of the bone marrow hole into the bone marrow hole so as to fix.

However, the conventional artificial joint structured in the manner mentioned above can effectively achieve a joint function, but on the other hand, has a problem in a fixing method. For example, in the conventional method of inserting the stem formed in the tapered rod shape or the like into the bone marrow hole and fixing it via the bone cement, not only the fixing operation is very troublesome and needs a lot of work, but also there is a risk that a fixing force is easily weakened due to an aging of tissues within the bone marrow hole or the like, so that it is hard to hold the fixing force for a long time. Further, in the conventional method of inserting the stem formed so as to fit to the inner surface of the bone marrow hole into the bone marrow hole so as to fix, not only it is very troublesome to manufacture the stem so that a cost is increased, but also in the case that a shape suitability with respect to the tissues within the bone marrow hole lacks, there is a risk of a stress concentration which has conventionally been a great problem in view of a design.

SUMMARY OF THE INVENTION

An object of the present invention is to provide an artificial joint which can clear up the conventional problems mentioned above once for all, and can be rapidly, securely and easily fixed while being suited to an inner surface of a bone marrow hole by a novel structure absolutely different from the conventional one.

That is, in accordance with a first aspect of the present invention, there is provided an artificial joint comprising:

a stem base portion 10 in which a desired head 2 and a desired socket 5 are in slidably contact with each other in a freely bending manner, stems 9 and 16 are respectively attached fitly to free ends of the head 2 and the socket 5, and the respective stems 9 and 16 have therein locking screws 14 freely screwing to move along axial directions thereof; and a pair of stem pieces 15 having an elasticity provided to protrude on both front portions of the stem base portion 10, wherein the locking screws 14 are forcedly inserted within the stem pieces 15 so as to expand them outward, thereby making them tightly contact with and fix to inner surfaces of bone marrow holes 19 and 21.

Accordingly, the present invention described in the first aspect mentioned above is structured such as to expand the stem pieces 15 outward so as to tightly contact with and fix to inner peripheral surfaces of the bone marrow holes 19 and 21 while screwing the locking screws 14 so as to be forcedly inserted into the both side stem pieces 15, and fitly attach the head 2 and the socket 5 respectively to the stem base portion 10 so as to be in slidable contact in a freely bending manner.

In accordance with a second aspect of the present invention, there is provided an artificial joint as recited in the first aspect, wherein cuboid-shaped fitting pieces 3 and 7 are protruded from the free ends of the head 2 and the socket 5, quadrangular fitting holes 12 are formed in the stem base portions 10 in such a manner as to correspond to the fitting pieces 3 and 7, and the fitting pieces 3 and 7 are fitted and attached to the fitting holes 12.

Accordingly, since the invention described in the second aspect mentioned above is structured such as to fit and attach the cuboid-shaped fitting pieces 3 and 7 to the quadrangular fitting holes 12, not only it is possible to freely select positions for fixing within the bone marrow holes 19 and 21 while rotating the stems 9 and 16 at every 90 degrees, but also it is possible to adjust fixing positions of the head 2 and the socket 5 while adjusting fits thereof, thereby freely adjusting a tension of a collateral ligament.

In accordance with a third aspect of the present invention, there is provided an artificial joint as recited in the first aspect or the second aspect, wherein a constriction member mounting groove 4 is formed in one of the head 2 and the socket 5 so as to constrict a tendon sheath of flexor muscle 22, and constriction member mounting holes 8 are formed in the other of the head 2 and the socket 5 so as to constrict a tendon sheath of extensor muscle 23.

Accordingly, since the invention described in the third aspect is structured such that desired constriction members 17 are mounted to the constriction member mounting groove 4 and holes 8 so as to constrict the tendon sheath of flexor muscle 22 and the tendon sheath of extensor muscle 23 to the head 2 and the socket 5 by the constriction members 17, it is possible to securely prevent a movement to the ulna side.

DESCRIPTION OF THE PREFERRED EMBODIMENT

A description will be given below of an embodiment in accordance with the present invention on the basis of one embodiment shown in the accompanying drawings.

Figure 1:
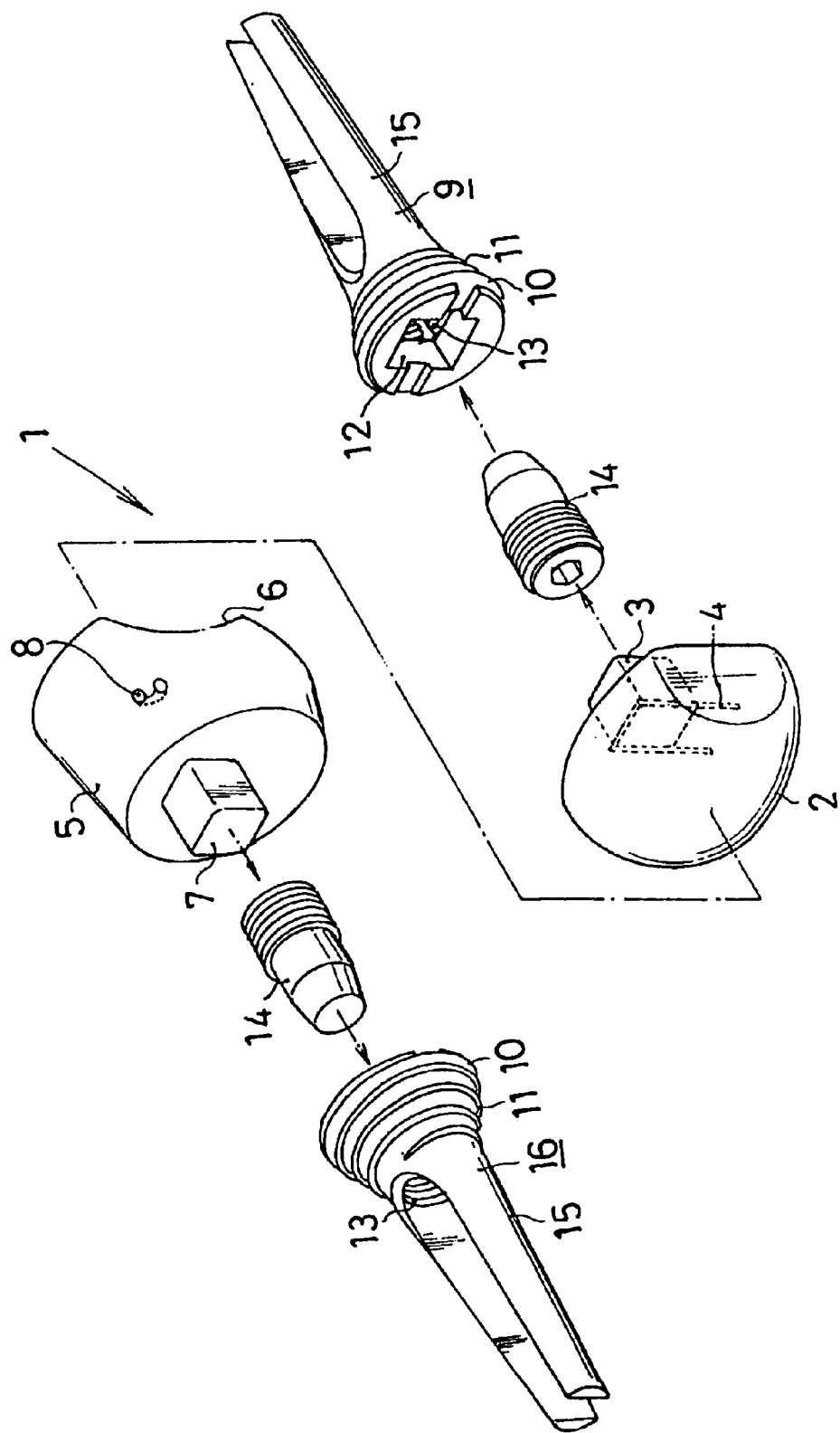
FIG. 1 is an exploded perspective view showing an embodiment in accordance with the present invention.
Figure 2:
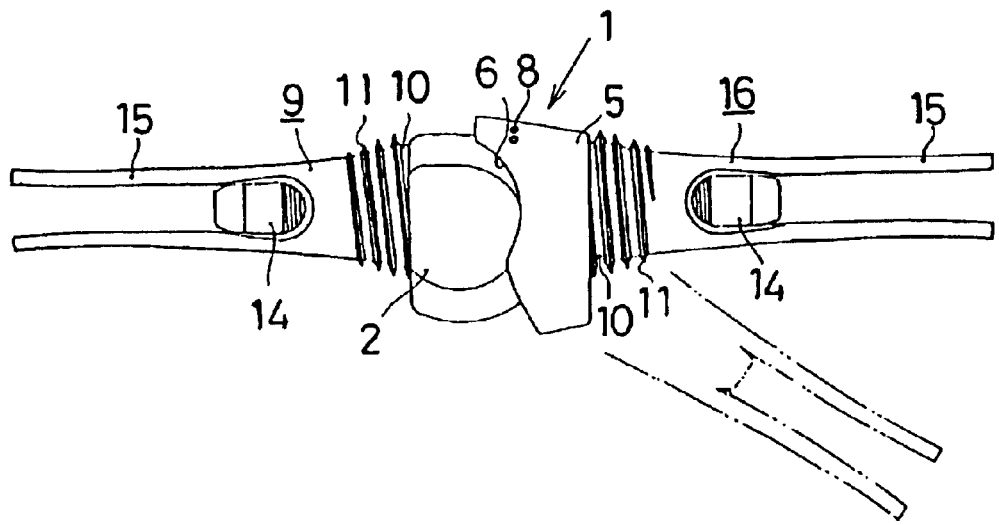
FIG. 2 is a side view showing an assembled state
Figure 3:
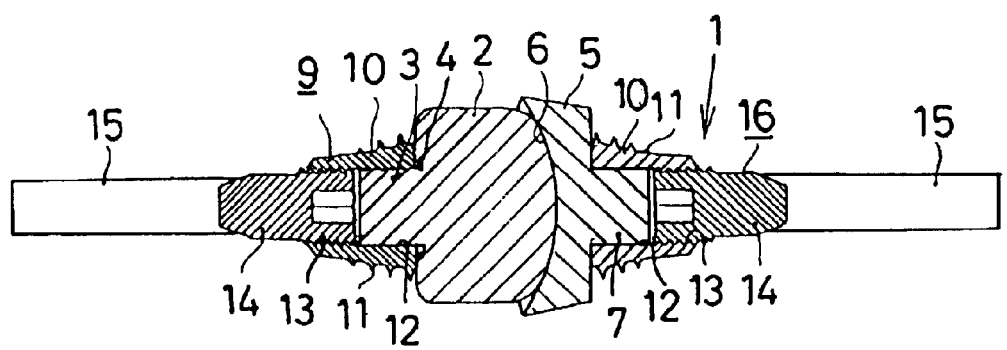
FIG. 3 is a horizontal cross sectional view of FIG. 2
Figure 4:
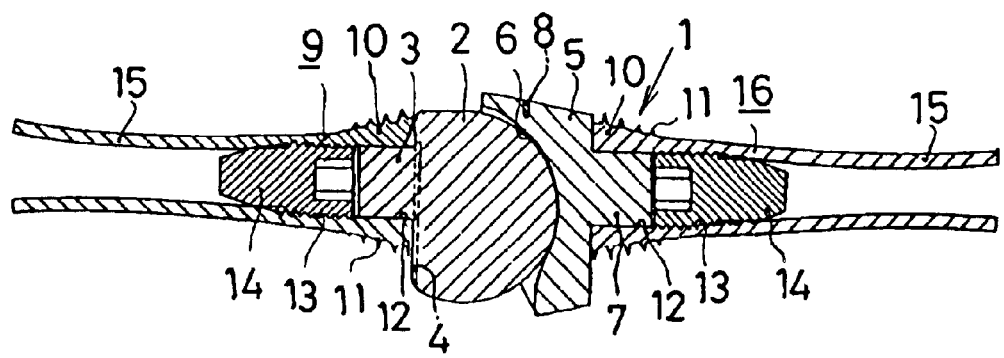
FIG. 4 is a vertical cross sectional view of FIG. 2.
Figure 5:
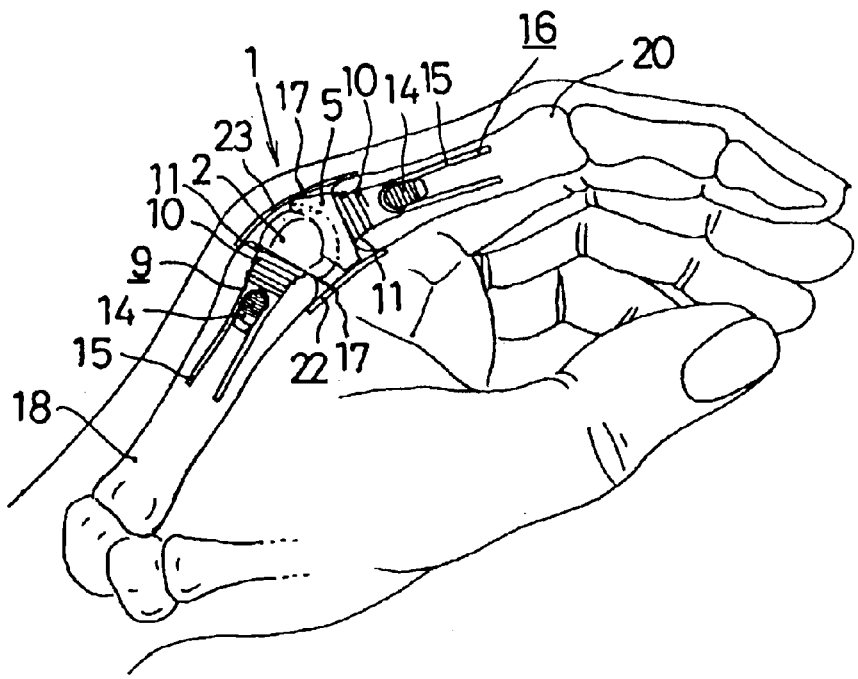
FIG. 5 is a side view showing a state of being used in an MP joint portion.
Figure 6:
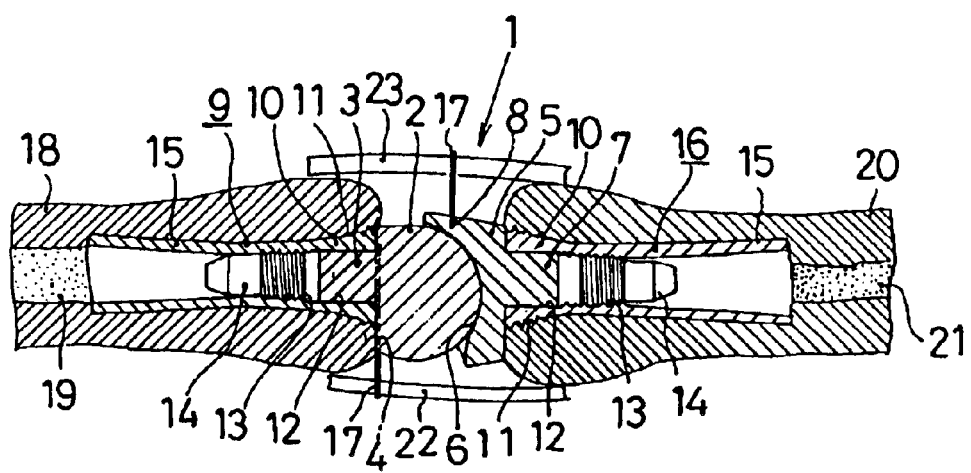
FIG. 6 is an enlarged cross sectional view of a main portion thereof.
Figure 7:
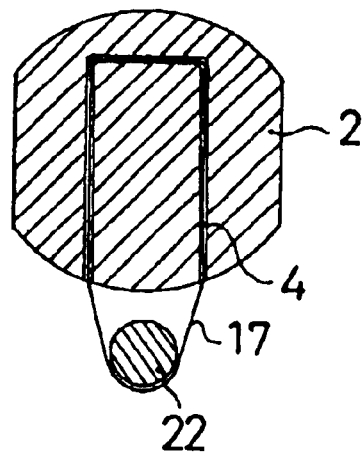
FIG. 7 is a horizontal cross sectional view showing a state that a tendon sheath of flexor muscle 22 is constricted to a head 2.
Figure 8:
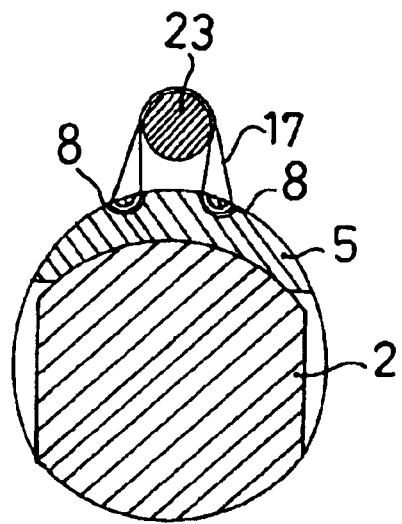
FIG. 8 is a horizontal cross sectional view showing a state that a tendon sheath of extensor muscle 23 is constricted to a head 5.

FIGS. 1 to 8 show one embodiment in accordance with the present invention. In the drawing, reference numeral 1 denotes an artificial knuckle joint, reference numeral 2 denotes a substantially semi-spherical head constituting the artificial knuckle joint 1, reference numeral 3 denotes an cuboid-shaped fitting piece provided to protrude on a back surface of the head 2, and reference numeral 4 denotes a constriction member mounting groove formed on the back surface of the head 2 along a base end portion of the fitting piece 3. Further, the head 2 is formed by a titanium alloy or a cobalt chrome alloy. Reference numeral 5 denotes a socket provided with a recess portion 6 in a spherical surface shape so as to slidably contact with the head 2 in a freely bending manner, reference numeral 7 denotes an cuboid-shaped fitting piece provided to protrude on a back surface of the socket 5, and reference numeral 8 denotes a pair of both side constriction member mounting holes formed in a top portion of the socket 5 in a communicating manner. Further, the socket 5 may be formed by a titanium alloy or a cobalt chrome alloy similarly to that of the head 2, however, is preferably formed by a plastic being excellent in an abrasion resistance, for example, an engineering plastic as typified by an ultra macromolecule polyethylene.

Reference numeral 9 denotes a stem for a metacarpal bone made of a titanium alloy or a cobalt chrome alloy to be fitly attachable to the head 2, reference numeral 10 denotes a stem base portion formed in a substantially truncated conical shape and constituting the metacarpal bone stem 9, reference numeral 11 denotes a screw thread formed on an outer peripheral surface of the stem base portion 10, reference numeral 12 denotes a quadrangular fitting hole having a desired depth formed in a base end of the stem base portion 10 so as to fit to the fitting piece 3 of the head 2, reference numeral 13 denotes a screw hole formed in a front end side of the stem base portion 10 along an axis thereof so as to communicate with the fitting hole 12, reference numeral 14 denotes a locking screw with a hexagonal hole having a desired length which is engaged with the screw hole 13 so as to freely screw to move, and reference numeral 15 denotes a pair of side tapered stem pieces having an elasticity and integrally provided to protrude on a front portion of the stem base portion 10 in such a manner as to correspond to the locking screw 14. The stem piece 15 can be freely expanded outward by screwing the locking screw 14 so as to forcedly insert, and an outer peripheral surface thereof is formed in a rough surface shape without finishing the surface. Reference numeral 16 denotes a stem for proximal phalanx structured such as to be fitly attachable to the socket 5. The proximal phalanx stem 16 is different from the metacarpal bone stem 9 in view of being formed in a slightly shorter shape than the metacarpal bone stem 9, and is the same in the other portions, and the same reference numerals denotes the same portions.

In addition, reference numeral 17 denotes a constriction member such as a wire or the like, reference numeral 18 denotes metacarpal bone, reference numeral 19 denotes a bone marrow hole in the metacarpal bone 18, reference numeral 20 denotes a proximal phalanx, reference numeral 21 denotes a bone marrow hole of the proximal phalanx 20, reference numeral 22 denotes a tendon sheath of flexor muscle, and reference numeral 23 denotes a tendon sheath of extensor muscle, respectively.

Next, a description will be given of a using method and an operation of an embodiment structured as mentioned above.

At first, a joint portion between the metacarpal bone 18 and the proximal phalanx 20 is cut so as to expose each of the bone marrow holes 19 and 21. Thereafter, the metacarpal bone stem 9 and the proximal phalanx stem 16 are respectively inserted into the corresponding bone marrow holes 19 and 21, and are screwed into opening end edges of the bone marrow holes 19 and 21 via the screw thread 11 of the stem base portion 10. Next, the front portions of the locking screws 14 are forcedly inserted into the stem pieces 15 in the both sides while being screwed respectively, and the outer peripheral surfaces of the stem pieces 15 are in tight contact with the inner peripheral surfaces of the bone marrow holes 19 and 21 so as to be fixed. At this time, since the stem pieces 15 have an elasticity, the stem pieces 15 can be easily and tightly contacted without giving a damage within the bone marrow holes 19 and 21, and further since the outer peripheral surfaces of the stem pieces 15 are formed in a rough surface shape, the bone can intrude into the depth of rough surface so as to generate a biological fixation with the elapse of time.

When the fixation of the metacarpal bone stem 9 and the proximal phalanx stem 16 is completed, the constriction members 17 such as the wires or the like are mounted to the head 2 and the socket 5 via the mounting groove 4 and the mounting holes 8, respectively. Next, the head 2 is fitly attached to the metacarpal bone stem 9 and the socket 5 is fitly attached to the proximal phalanx stem 16, respectively by fitting the fitting pieces 3 and 7 to the corresponding fitting holes 12, and further both are slidably contacted in a freely bending manner. At this time, since the head 2 and the socket 5 are structured such that the fitting pieces 3 and 7 are respectively fitted and attached to the fitting holes 12 in the metacarpal bone stem 9 and the proximal phalanx stem 16, not only it is possible to freely select the fixing positions in the bone marrow holes 19 and 21 while rotating the metacarpal bone stem 9 and the proximal phalanx stem 16 at every 90 degrees, respectively, but also it is possible to adjust the fixing positions of the head 2 and the socket 5 while suitably adjusting fits thereof so as to freely adjust a tension of collateral ligament. Thereafter, the tendon sheath of flexor muscle 22 is constricted to the head 2 via the constriction member 17 and the tendon sheath of extensor muscle 23 is constricted to the socket 5 (refer to FIGS. 6 to 8). At this time, since the tendon sheath of flexor muscle 22 and the tendon sheath of extensor muscle 23 are respectively constricted to the head 2 and the socket 5, it is possible to securely prevent a movement to the ulna side and it is possible to effectively prevent an extension disability of the MP joint caused by a failure of the sutures in the tendon sheath of extensor muscle 23 or the like. When the constriction of the tendon sheath of flexor muscle 22 and the tendon sheath of extensor muscle 23 is finished, an operation is completed by repairing the ligament and others in accordance with the known method (refer to FIG. 5).

In this case, in the embodiment mentioned above, the head 2 and the socket 5 are made in a spherical joint structure, however, they are not limited to this, and may be formed in a hinge joint structure. Further, the structure is made such that the tendon sheath of flexor muscle 22 is constricted to the head 2 and the tendon sheath of extensor muscle 23 is constricted to the socket 5, respectively, however, on the contrary, the structure may be made such that the tendon sheath of flexor muscle 22 is constricted to the socket 5 and the tendon sheath of extensor muscle 23 is constricted to the head 2, respectively. Further, the mounting operation of the constriction members 17 are executed via the mounting groove 4 and the mounting holes 8, however, it is not limited to this, and the constriction members 17 may be mounted via the other known mounting structures. In this case, the embodiment mentioned above shows the artificial knuckle joint 1 for the MP joint, however, the structure is not limited to this, for example, the present invention can be also applied to an artificial knuckle joint for a PIP joint or an artificial elbow joint.

Since the present invention described in the first aspect is structured as mentioned above, it is possible to expand the stem pieces 15 outward so as to tightly contact with and fix to inner peripheral surfaces of the bone marrow holes 19 and 21 while screwing the locking screws 14 so as to forcedly insert into the both side stem pieces 15, and fit and attach the head 2 and the socket 5 respectively to the stem base portions 10 so that both are in slidably contact in a freely bending manner. Therefore, not only it is possible to rapidly, securely and easily perform the fixing operation, but also it is possible to smartly, easily and securely mount the head 2 and the socket 5 directly to the stems 9 and 16 in a very natural style without interfering with the screwed locking screw 14. Further, since it is possible to insert another stem by utilizing the gap generated by the outer expansion of the stems 9 and 16 as mentioned above, for example, it is possible to operate the artificial knuckle joint for the PIP joint or the like to the artificial knuckle joint for the MP joint of the same finger one by one. Furthermore, since the structure is simple, not only it is possible to easily manufacture, but also it is possible to inexpensively provide the structure.

Since the present invention described in the second aspect is structured as mentioned above, not only it is possible to freely select positions for fixing within the bone marrow holes 19 and 21 while rotating the stems 9 and 16 at every 90 degrees, but also it is possible to adjust fixing positions of the head 2 and the socket 5 while adjusting fits, thereby freely adjusting a tension of a collateral ligament.

Since the present invention described in the third aspect is structured as mentioned above, the desired constriction members 17 are mounted to the constriction member mounting portions 4 and 8 so as to constrict the tendon sheath of flexor muscle 22 and the tendon sheath of extensor muscle 23 to the head 2 and the socket 5 by the constriction members 17, whereby it is possible to securely prevent a movement to the ulna side, and further it is possible to effectively prevent the extension disability of the MP joint or the like caused by the failure of the sutures of the tendon sheath of flexor muscle 22 and the tendon sheath of extensor muscle 23.

What is claimed is:

1. An artificial joint comprising:
    a head (2) having a spherical convex surface at one end and a first fitting piece (3) with a quadrangular configuration in cross section at the other end;
    a socket (5) having a spherical concave surface (6) at one end and a second fitting piece (7) with a quadrangular configuration in cross section at the other end, said head (2) and said socket (5) being interconnected so that said spherical convex and concave surfaces slidably contacts with each other;
    a first stem (9) having at one end a first stem base portion (10) provided with a first fitting hole (12) having a quadrangular configuration in cross section and a first threaded hole (13) and at the other end a first pair of stem pieces (15) which extend from the first stem base portion (16) and are spaced substantially in parallel with each other, said first fitting piece (3) of said head (2) being engaged with said first fitting hole (12);
    a second stem (16) having at one end a second stem base portion (10) provided with a second fitting hole (12) having a quadrangular configuration in cross section and a second threaded hole (13) and at the other end a second pair of stem pieces (15) which extend from said second stem base portion (10) and are spaced substantially in parallel with each other, said second fitting piece (7) of said socket (5) being engaged with said second filling hole (12);
    a first locking screw (14) forcedly screwed into said first threaded hole (13) so as to expand said first pair of stem pieces (15) outwardly; and
    a second locking screw (14) forcedly screwed into said second threaded hole (13) so as to expand said second pair of stem pieces (15) outwardly,
    wherein said head (2) is provided with a first constriction member mounting structure, and
    said socket (5) is provided with a second constriction member mounting structure;
    a first constriction member, mounted to said first constriction member mounting structure, to constrict a first tendon sheath; and
    a second constriction member, mounted to said second constriction member mounting structure, to constrict a second tendon sheath.

2. The artificial joint of claim 1, wherein said constriction member mounting structure includes a constriction member mounting groove (4) formed in one of the head (2) and the socket (5) so as to constrict a tendon sheath of flexor muscle (22), and a constriction member mounting holes (8) formed in the other of the head (2) and the socket (5) so as to constrict a tendon sheath of extensor muscle (23).

3. The artificial joint of claim 1, wherein a constriction member mounting groove (4) is formed in one of the head (2) and the socket (5) so as to constrict a tendon sheath of flexor muscle (22), and a constriction member mounting holes (8) are formed in the other of the head (2) and the socket (5) so as to constrict a tendon sheath of extensor muscle (23).

4. The artificial joint of claim 1, wherein either of said first or said second constriction member mounting structure comprises a constriction member mounting groove; and
    the other of either said first or said second constriction member mounting structure comprises constriction member mounting holes (8).

5. The artificial joint of claim 4, wherein said constriction member mounting groove on a back surface of said head (2) along a base end portion of said first fitting piece (3).

6. The artificial joint of claim 4, wherein said constriction member mounting holes (8) comprise a plurality of side constriction member mounting holes formed in a top portion of said socket (5) in a communicating manner.

7. The artificial joint of claim 1, wherein one of either said head (2) or said socket (5) is provided with a first constriction member mounting groove (4) while the other of either said head (2) or said socket (5) is provided with a plurality of constriction member mounting holes (8).

8. The artificial joint of claim 1, wherein an outer surface of said stem pieces (15) are textured to promote bone growth fixation to said outer surface.

9. The artificial joint of claim 1, wherein said first and said second constriction members comprise wires.

10. The artificial joint of claim 1, wherein said first and said second constriction members prevent movement of said artificial joint to an ulna side of a finger.

11. An artificial joint comprising:
- a head comprising a hemi-spherical convex surface and a first fitting piece opposite said hemi-spherical convex surface;
- a socket comprising a hemi-spherical concave surface and a second fitting piece opposite said hemi-spherical concave surface, said head and said socket being interconnected so that said hemi-spherical convex and concave surfaces slidably contact with each other;
- a first stem comprising at one end a first stem base portion provided with a first fitting hole and at the other end a first pair of outwardly biased stem pieces which extend from the first stem base portion and are spaced substantially in parallel with each other, said first fitting piece of said head being engaged with said first fitting hole and wherein said first pair of stem pieces are outwardly expandable;
- a second stem having at one end a second stem base portion provided with a second fitting hole and at the other end a second pair of outwardly biased stem pieces which extend from said second stem base portion and are spaced substantially in parallel with each other, said second fitting piece of said socket being engaged with said second fitting hole, and wherein said second pair of stem pieces are outwardly expandable;
- a first constriction member, attached to said head, to constrict a first tendon sheath; and
- a second constriction member, attached to said socket, to constrict a second tendon sheath.

12. The artificial joint of claim 11, wherein said first constriction member is attached to a first constriction member mounting structure formed on said head, and
   said second constriction member is attached to a second constriction member mounting structure formed on said socket.

13. The artificial joint of claim 12, wherein either of said first or said second constriction member mounting structure comprises a constriction member mounting groove; and
   the other of either said first or said second constriction member mounting structures comprises constriction member mounting holes.

14. The artificial joint of claim 11, wherein an outer surface of said stem pieces are textured to promote bone growth fixation to said outer surface.

* * * * *